(12) United States Patent
Xie et al.

(10) Patent No.: US 8,778,417 B2
(45) Date of Patent: Jul. 15, 2014

(54) ANTI-TUMOR PLANT-MEDICAMENT SUSTAINED-RELEASE TABLET OF ELEMENE

(75) Inventors: Tian Xie, Dalian (CN); Haizhu Fan, Dalian (CN); Xiaori Zhan, Dalian (CN); Chenglu Li, Dalian (CN); Zhaowu Zeng, Dalian (CN)

(73) Assignee: Tian Xie, Dalian (CN)

( * ) Notice: Subject to any disclaimer, the term of this patent is extended or adjusted under 35 U.S.C. 154(b) by 0 days.

(21) Appl. No.: 13/697,138

(22) PCT Filed: Apr. 8, 2011

(86) PCT No.: PCT/CN2011/072530
§ 371 (c)(1),
(2), (4) Date: Nov. 9, 2012

(87) PCT Pub. No.: WO2011/140872
PCT Pub. Date: Nov. 17, 2011

(65) Prior Publication Data
US 2013/0059922 A1    Mar. 7, 2013

(30) Foreign Application Priority Data
May 10, 2010 (CN) .......................... 2010 1 0165908

(51) Int. Cl.
*A01N 65/00* (2009.01)
(52) U.S. Cl.
USPC ....................................................... 424/725
(58) Field of Classification Search
None
See application file for complete search history.

(56) References Cited

FOREIGN PATENT DOCUMENTS

| CN | 1408347 A | 4/2003 |
|---|---|---|
| CN | 1726906 A | 2/2006 |
| CN | 101125124 A | 2/2008 |
| CN | 101402543 A | 4/2009 |

OTHER PUBLICATIONS

An International Search Report, dated Jul. 14, 2011, issued in Internatonal Application No. PCT/CN2011/072530.

*Primary Examiner* — Michael Meller
(74) *Attorney, Agent, or Firm* — Lowe Hauptman & Ham, LLP

(57) ABSTRACT

Disclosed is an anti-tumor plant-medicament sustained-release tablet of elemene which comprises an elemene as an active component and is prepared by formulation of the elemene, a sustained-release agent, a bulking agent, a disintegrating agent, a binder and a lubricant, each component above-mentioned being in the following weight composition: the elemene 10%-15%, the sustained-release agent 3%-15%, the bulking agent 45%-70%, the disintegrating agent 3%-8%, the binder 1%-10%, and the lubricant 1%-8%. The sustained-release tablet of elemene provided in the invention has properties of expansion and adhesion, which in turn enables extending the retention time of the drug on upper and middle sections of the gastrointestinal tract. Therefore, the tablet may be taken b.i.d.×3, in order to attain reduction in fluctuation of the plasma concentration, maintain effective plasma concentration for a longer period, and reduce the irritation on the gastrointestinal tract. The skeleton-type sustained- and controlled-release formulation has advantages of low cost, easy control, and easy industrialized production.

10 Claims, 1 Drawing Sheet

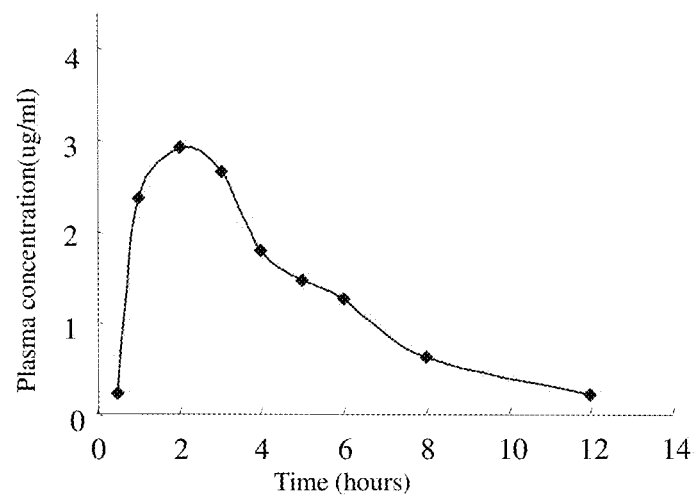

ANTI-TUMOR PLANT-MEDICAMENT SUSTAINED-RELEASE TABLET OF ELEMENE

RELATED APPLICATIONS

The present application is a National Stage of PCT/CN2011/072530 filed Apr. 8, 2011, and claims priority from, Chinese Application No. 201010165908.X filed May 10, 2010.

FIELD OF THE INVENTION

The present invention relates to an anti-tumor plant-medicament sustained-release tablet of elemene.

BACKGROUND OF THE INVENTION

Elemene is a natural medical substance extracted firstly in China from the rhizomes of Wen Yu Jin (*Curcuma wenyujin*), a plant from Zingiberaceae, also known as wenchow turmeric rhizome, serving as an anticancer agent with a novel structure. Elemene is found extensively in a wide variety of Traditional Chinese herbs, such as Radix ginseng, Largehead atractylodes rhizome, *Syzygium aromaticum, Chloranthus fortunei, Chioranthus multistachys, Commiphora myrrha, Divaricate saposhnikovia* Root, etc. Chemical name for elemene is 1-methyl-1-vinyl-2,4-disopropenylcyclohexane, with the molecular formula: $C_{15}H_{24}$. Four isomers are found in the elemene: α-elemene, β-elemene, γ-elemene and Δ-elemene, with the primary component of the anti-tumor plant-medicament elemene being β-elemene. The chemical structural formula for the elemene is as follows:

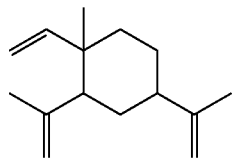

Many literatures have reported the methods for preparing elemene, which generally comprise extracting and refining elemene from the plants such as Zedoary turmeric, etc.; or isolating elemene directly from Zedoary turmeric oil. Such methods are described in Chinese patent applications: CN1686975A, CN1651366A and CN1200266A.

The elemene had been approved as a Chinese new drug of national Class II in December, 1993. The anti-cancer efficacy of the elemene had been verified by the Ministry of Health of the People's Republic of China in February, 1994. Elemene is the first anti-tumor plant-medicament in the world which contains no toxic groups such as epoxy, nitro, anthracene ring, benzene ring, etc. Thus, it has no toxicity, a mild adverse reaction, an established efficacy as well as an excellent price/performance ratio. Moreover, it had unique properties such as crossing the blood-brain barrier and the blood-bone barrier. Elemene is a volatile oil and thus exhibits stronger volatility and liposolubility. It is clinically used mainly in treatment of various cancers such as esophageal cancers, lung cancers, brain tumors, hepatocarcinomas, cervical cancers, cancerous chest, ascite, etc. The elemene emulsion injection made from elemene as feedstock has been used widely in clinics and exhibited good efficacy in clinical environments. Presently, there are two types of administration routes for elemene, i.e., injection and oral administration, and correspondingly two types of dosage forms, i.e., elemene injection and elemene oral emulsion. The elemene formulations in the art are all rapid-release formulations with frequent dosing times and a short biological half-life, thus leading to more significant fluctuation in the plasma concentration. Oral administration of elemene exhibits a significant first-pass effect and thus a low bioavailability. Intravenous administration of elemene is liable to induce local phlebitis, drug fever, thrombocytopenia, pain at the infusion site and digestive tract reactions. For the preparation of elemene formulations, see Chinese patent applications: CN1244389A, CN1508176A, CN1076613A, CN1507857A, CN101461793A, CN1221607A and CN1451377A. However, formulations disclosed in the above patents exhibit more significant adverse reactions when used clinically, and have disadvantages with respects of storage and anti-cancer activities.

Heretofore, there is no patent literature about research on an anti-tumor plant-medicament sustained-release tablet of elemene. Also there is no patent literature about use of elemene in a dosage form of a sustained-release tablet for treating conditions such as esophageal cancers, lung cancers, brain tumors, hepatocarcinomas, cervical cancers, cancerous chest, ascite, etc.

SUMMARY OF THE INVENTION

The technical problem to be addressed by the invention is how to obtain a sustained-release formulation of the anti-tumor plant-medicament elemene, which enables reduction in the fluctuation of the plasma concentration, maintaining effective plasma concentration for a longer period, and reduction in the irritation on the gastrointestinal tract.

To solve the above-mentioned technical problems, the following technical scheme is provided in the invention:

An anti-tumor plant-medicament sustained-release tablet of elemene, which comprises an elemene as an active component and is prepared by formulation of the elemene, a sustained-release agent, a bulking agent, a disintegrating agent, a binder and a lubricant, each component above-mentioned being in the following weight composition:

| | |
|---|---|
| elemene | 10%-15% |
| sustained-release agent | 3%-15% |
| bulking agent | 45%-70% |
| disintegrating agent | 3%-8% |
| binder | 1%-10% |
| lubricant | 1%-8%, | the bulking agent in the invention is selected from the group consisting of hydroxypropyl methyl cellulose (HPMC-4M, HPMC-15M, HPMC-100M, etc.), polyvinyl pyrollidone (PVP), ethylcellulose (EC), methyl cellulose (MC), hydroxyethyl cellulose (HEC), sodium carboxymethyl cellulose (CMC-Na) and any combination of thereof;

the bulking agent in the invention is selected from the group consisting of microcrystalline cellulose, β-cyclodextrin, lactose, calcium sulphate, compressible starch and any combination of thereof;

the disintegrating agent in the invention is sodium carboxymethyl starch;

the binder in the invention is selected from one of the following: aqueous solution of polyvinyl pyrollidone with a mass concentration of 1%-10%, ethanolic solution of polyvinyl pyrollidone with a mass concentration of 1%-10%, aqueous solution of ethylcellulose with a mass concentration of 1%-10%, ethanolic solution of ethylcellulose with a mass concentration of 1%-10%, aqueous solution of hydroxypropyl methyl cellulose with a mass concentration of 1%-10%, aqueous solution of starch with a mass concentration of 1%-10%. The mass concentration set forth in the invention denotes percent content of the mass of a component per volume of a mixture. For example, the mass concentration of the aqueous solution of polyvinyl pyrollidone is calculated by the equation below:

$$\text{Mass concentration for the aqueous solution of polyvinyl} = \frac{\text{weight }(w)\text{ of polyvinyl pyrollidone}}{\text{volume }(v)\text{ of the aqueous solution of polyvinyl pyrollidone}} \times 100\%$$

It is not especially indicated herein that the mass concentration "%" denote the weight percent (w/w).

The lubricant in the invention is selected from one of the following: magnesium stearate, colloidal silicon dioxide, and talc.

The elemene in the invention is a mixture of β-elemene, gamma-elemene and delta-elemene complying with the Chinese Quality Standard for Western Medicine WS-048 (X-040)-96, or is a β-elemene monomer.

Further, the sustained-release agent in the invention is preferably hydroxypropyl methyl cellulose or methyl cellulose.

Further, the bulking agent in the invention is preferably microcrystalline cellulose or the combination of microcrystalline cellulose with either or both of β-cyclodextrin and lactose.

Further, the binder in the invention is preferably an aqueous solution of starch with a weight concentration of 1%10%.

Further, the lubricant in the invention is preferably colloidal silicon dioxide.

Further, it is preferred in the invention that the sustained-release tablet of elemene is obtained by formulation of the components in the following weight composition, wherein the sustained-release agent is hydroxypropyl methyl cellulose or methyl cellulose; the bulking agent is selected from one of the following: microcrystalline cellulose, the combination of microcrystalline cellulose with lactose, and the combination of microcrystalline cellulose with β-cyclodextrin and lactose:

| | |
|---|---|
| elemene | 10%-15% |
| sustained-release agent | 3%-15% |
| bulking agent | 45%-70% |
| sodium carboxymethyl starch | 3%-8% |
| aqueous solution of starch with a concentration of 1-10% | 1%-10% |
| colloidal silicon dioxide | 1%-8%. |

Furthermore, it is preferable that the weight ratio of microcrystalline cellulose to lactose is from 3:1 to 1:1 when the bulking agent in the invention is the combination of microcrystalline cellulose with lactose; and it is preferable that the ratio of the total mass of microcrystalline cellulose and lactose to the mass of β-cyclodextrin is no less than 3:1 when the bulking agent is the combination of microcrystalline cellulose with lactose and β-cyclodextrin.

Furthermore, it is preferred in the invention that the sustained-release tablet of elemene is obtained by formulation of the components in the following weight composition, wherein the sustained-release agent is hydroxypropyl methyl cellulose or methyl cellulose; the bulking agent is selected from one of the following: microcrystalline cellulose, the combination of microcrystalline cellulose with lactose, and the combination of microcrystalline cellulose with β-cyclodextrin and lactose:

| | |
|---|---|
| elemene | 10%-12% |
| sustained-release agent | 3%-8% |
| bulking agent | 61%-68% |
| sodium carboxymethyl starch | 3%-6% |
| aqueous solution of starch with a concentration of 8% | 5%-8% |
| colloidal silicon dioxide | 5%-8%. |

Also provided in the invention is a method for preparing the above-mentioned sustained-release tablet of elemene, in which the sustained-release tablet of elemene is prepared by the following procedure: weighing each component in the weight ratios set forth above in the invention; firstly mixing the bulking agent, the sustained-releasing agent and the disintegrating agent into homogeneity; then adding the binder for granulation; the resultant granulates being dried at the temperature of from 40° C. to 70° C., finished, sprayed evenly with the elemene, sealed to saturate for 20-60 minutes, dusted again with the lubricant, mixed homogenously, and pressed into tablets, thus resulting in said sustained-releasing tablets of elemene.

As compared to the prior-art, the sustained-release tablet of elemene provided in the invention has properties of expansion and adhesion, which in turn enables extending the retention time of the drug on upper and middle sections of the gastrointestinal tract. Therefore, the tablet may be taken b.i.d.×3 (twice a day, three tablets for one time), in order to attain reduction in fluctuation of the plasma concentration, maintain effective plasma concentration for a longer period, and reduce the irritation on the gastrointestinal tract. The skeleton-type sustained- and controlled-release formulation has advantages of low cost, easy control, and easy industrialized production.

BRIEF DESCRIPTION OF THE DRAWINGS

FIG. 1 is a curve of an average plasma concentration vs time (n=6) obtainable from Example 9 after oral administration of the sustained-release tablet of elemene in rabbits.

DETAILED DESCRIPTION OF THE INVENTION

While the technical solution of the present invention will be further illustrated by the following specific Examples, the protection scope of the invention is not to be limited thereto:

Example 1

| | | | | Prescription I | | | |
|---|---|---|---|---|---|---|---|
| Components | Microcrystalline cellulose | Lactose | Sodium carboxymethyl starch | Hydroxypropyl methyl cellulose K-15M | Colloidal silicon dioxide | aqueous solution of starch with 8% | β-elemene |
| Amount (g) | 25 | 10 | 2 | 2 | 4 | 3 | 6 |

First, microcrystalline cellulose, lactose, sodium carboxymethyl starch, hydroxypropyl methyl cellulose were mixed homogenously. Then, the aqueous solution of starch with a mass concentration of 8% was added in quantum libet. The resultant mixture was granulated through a screen of 14 mesh (that is, a screen with pore size of 1180 μm). The resultant granulates were dried at 50° for 6 hours, screened through a screen of 16 mesh (that is, a screen with pore size of 1000 μm), sprayed with the elemene, sealed, saturated for 30 minutes, then dusted with colloidal silicon dioxide, and finally pressed into the tablets.

Example 2

| | | | | Prescription II | | | |
|---|---|---|---|---|---|---|---|
| Components | Microcrystalline cellulose | Lactose | Sodium carboxymethyl starch | Hydroxypropyl methyl celluloseK-15M | Colloidal silicon dioxide | aqueous solution of starch with 8% | β-elemene |
| Amount (g) | 25 | 10 | 2 | 4.25 | 4.2 | 4 | 6 |

First, microcrystalline cellulose, lactose, sodium carboxymethyl starch, hydroxypropyl methyl cellulose were mixed homogenously. Then, 8% of the aqueous solution of starch was added in quantum libet. The resultant mixture was granulated through a screen of 14 mesh. The resultant granulates were dried at 50° for 6 hours, screened through a screen of 16 mesh, sprayed with the elemene, sealed, saturated for 30 minutes, then dusted with colloidal silicon dioxide, and finally pressed into the tablets.

Example 3

| | | | | Prescription III | | | |
|---|---|---|---|---|---|---|---|
| Components | Microcrystalline cellulose | Lactose | Sodium carboxymethyl starch | Methyl cellulose | Colloidal silicon dioxide | aqueous solution of starch with 8% | β-elemene |
| Amount (g) | 25 | 10 | 2 | 2 | 4 | 3 | 6 |

First, microcrystalline cellulose, lactose, sodium carboxymethyl starch, methyl cellulose were mixed homogenously. Then, 8% of the aqueous solution of starch was added in quantum libet. The resultant mixture was granulated through a screen of 14 mesh. The resultant granulates were dried at 50° for 6 hours, screened through a screen of 16 mesh, sprayed with the elemene, sealed, saturated for 30 minutes, then dusted with colloidal silicon dioxide, and finally pressed into the tablets.

Example 4

Prescription IV

| Components | Microcrystalline cellulose | Lactose | Sodium carboxymethyl starch | Methyl cellulose | Colloidal silicon dioxide | aqueous solution of starch with 8% | β-elemene |
|---|---|---|---|---|---|---|---|
| Amount (g) | 25 | 10 | 2 | 4.25 | 4 | 4 | 6 |

First, microcrystalline cellulose, lactose, sodium carboxymethyl starch, methyl cellulose were mixed homogenously. Then, 8% of the aqueous solution of starch was added in quantum libet. The resultant mixture was granulated through a screen of 14 mesh. The resultant granulates were dried at 50° for 6 hours, screened through a screen of 16 mesh, sprayed with the elemene, sealed, saturated for 30 minutes, then dusted with colloidal silicon dioxide, and finally pressed into the tablets.

Example 5

Prescription V

| Components | Microcrystalline Cellulose | Sodium carboxymethyl starch | Hydroxypropyl methyl cellulose K-15M | Colloidal silicon dioxide | aqueous solution of starch with 8% | β-elemene |
|---|---|---|---|---|---|---|
| Amount (g) | 35 | 3.25 | 2 | 4 | 3 | 6 |

First, microcrystalline cellulose, sodium carboxymethyl starch, hydroxypropyl methyl cellulose were mixed homogenously. Then, 8% of the aqueous solution of starch was added in quantum libet. The resultant mixture was granulated through a screen of 14 mesh. The resultant granulates were dried at 50° for 6 hours, screened through a screen of 16 mesh, sprayed with the elemene, sealed, saturated for 30 minutes, then dusted with colloidal silicon dioxide, and finally pressed into the tablets.

Example 6

Prescription VI

| Components | Microcrystalline Cellulose | Sodium carboxymethyl starch | Hydroxypropyl methyl cellulose K-15M | Colloidal silicon dioxide | aqueous solution of starch with 8% | β-elemene |
|---|---|---|---|---|---|---|
| Amount (g) | 35 | 3.25 | 4.25 | 4 | 4 | 6 |

First, microcrystalline cellulose, sodium carboxymethyl starch, hydroxypropyl methyl cellulose were mixed homogenously. Then, 8% of the aqueous solution of starch was added in quantum libet. The resultant mixture was granulated through a screen of 14 mesh. The resultant granulates were dried at 50° for 6 hours, screened through a screen of 16 mesh, sprayed with the elemene, sealed, saturated for 30 minutes, then dusted with colloidal silicon dioxide, and finally pressed into the tablets.

Example 7

Prescription VII

| Components | Micro-crystalline cellulose | β-cyclodextrin | Lactose | Sodium carboxymethyl starch | Hydroxypropyl methyl cellulose K-15M | Colloidal silicon dioxide | aqueous solution of starch with 8% | β-elemene |
|---|---|---|---|---|---|---|---|---|
| Amount (g) | 27.5 | 10 | 15 | 3 | 6.4 | 6 | 6 | 9 |

First, microcrystalline cellulose, β-cyclodextrin, lactose, sodium carboxymethyl starch, hydroxypropyl methyl cellulose were mixed homogenously. Then, 8% of the aqueous solution of starch was added in quantum libet. The resultant mixture was granulated through a screen of 14 mesh. The resultant granulates were dried at 50° for 6 hours, screened through a screen of 16 mesh, sprayed with the elemene, sealed, saturated for 30 minutes, then dusted with colloidal silicon dioxide, and finally pressed into the tablets.

Example 8

Release Rate Test

The specimen content resulting from the release rate test was determined by high performance liquid chromatography (HPLC). In the elemene concentration ranging from 4-36 µg·mL$^{-1}$ of the test, the absorbance is in good linear relation with the concentration with good stability and reproducibility.

The in vitro release experiment on the sustained-release tablets of elemene (Examples 1-7) was performed as follows: According to the rotating basket method, the first method in In Vitro Release Rate test, in Pharmacopoeia of Peoples Republic of China, 2005 Edition, the release medium is 900 mL 1% Tween-20 solution, at the temperature of (37±1)°, with a rotatory speed of 100 rpm (r·min$^{-1}$). 10 mL of the specimens were sampled at 1, 2, 4, 6, 8, 10, 12 and 16 hour respectively (simultaneously supplemented with the equal volume of the isothermal medium) and filtered. 1 mL of the filtrate was placed into a 10 mL volumetric flask, diluted with the 1% Tween-20 solution to the scale, and shaken to homogeneity. 5 µL of the resultant mixture was injected into the high performance liquid chromatography apparatus, and the area of the primary peak was recorded. Reference standard β-elemene in quantum libet was weighed precisely, dissolved in the 1% Tween-20 solution, diluted into a solution of about 25 µg/mL, and assayed in the same way as above. According to the external standard method, the accumulative release rate for each tablet was calculated respectively at different time-points, and the experimental result was shown in the table below:

|  |  | Time (h) | | | | | | | |
|---|---|---|---|---|---|---|---|---|---|
|  |  | 1 | 2 | 4 | 6 | 8 | 10 | 12 | 16 |
| Release Rate (%) | Example 1 | 26 | 33.4 | 43.2 | 51.6 | 60.4 | 65.6 | 70.0 | 81.0 |
|  | Example 2 | 20.3 | 27.2 | 38.1 | 46.6 | 53.0 | 59.7 | 67.8 | 79.2 |
|  | Example 3 | 14.9 | 25.1 | 42.5 | 48.9 | 57.5 | 64.1 | 72.3 | 82.5 |
|  | Example 4 | 18.4 | 29.2 | 45.0 | 52.3 | 60.3 | 66.8 | 74.5 | 84.0 |
|  | Example 5 | 26.6 | 33.8 | 43.5 | 49.5 | 58.4 | 65.6 | 71.9 | 79.0 |
|  | Example 6 | 16.9 | 23.4 | 36.9 | 49.1 | 51.1 | 62.6 | 68.0 | 78.9 |
|  | Example 7 | 20 | 28.5 | 44.2 | 53.6 | 62.4 | 68.6 | 75.2 | 86.2 |

As can be seen from the above test result, the cumulative release amounts of the sustained-release tablets of elemene from Examples 5-7 at the three time-points of 2, 6, and 12 hour account for about 30%, 50%, 70% of the labeled amount with good release effect, substantially meeting with the criteria for the sustained-release table in Pharmacopoeia of Peoples Republic of China.

Example 9

Pharmacokinetic Test

The specimen content resulting from the pharmacokinetic test was determined by high performance liquid chromatography (HPLC). In the elemene concentration ranging from 0.2-25.6 µg·mL$^{-1}$ of the test, there is a good linear relation with a recovery rate of greater than 95.20%.

The in vivo pharmacokinetic experiment on the animals in the invention was performed as follows: Six of New Zealand rabbits were each administrated every day with 3 of the sustained-release tablets obtainable from Example 5. 2 mL of ear venous blood was collected respectively at 0.5, 1, 2, 3, 4, 5, 6, 8 and 12 hours after administration, placed into a centrifuge tube, and centrifuged at 5000 r·min$^{-1}$ for 10 min, separating the supernatant. 0.4 mL of the supernatant was introduced into 0.8 mL of acetonitrile, vortexed for 3 min, and centrifuged at 15000 r·min$^{-1}$ for 10 min. The resultant supernatant was pipetted and assayed on the high performance liquid chromatography apparatus. The result indicates that oral administering 3 of the tablets every day can attain the desired plasma concentration and maintain the release of the drug for 12 hours (see FIG. 1).

Disclosed above are merely several specific embodiments of the present invention. However, the present invention should not be limited to these embodiments and any of variations thereof that can be contemplated by those skilled in the art should fall within the claimed scope of the instant invention.

The invention claimed is:
1. A sustained-release tablet consisting essentially of:
  10%-15% by weight of elemene in the total tablet;
  3%-15% by weight of a sustained-release agent in the total tablet;

45%-70% by weight of a bulking agent in the total tablet;
3%-8% by weight of a disintegrating agent in the total tablet;
1%-10% by weight of a binder in the total tablet; and
1%-8% by weight of a lubricant in the total tablet;
wherein said sustained-release agent is selected from the group consisting of hydroxypropyl methyl cellulose, polyvinyl pyrollidone, ethylcellulose, methyl cellulose, hydroxyethyl cellulose, sodium carboxymethyl cellulose and mixtures thereof;
said bulking agent is selected from the group consisting of microcrystalline cellulose, β-cyclodextrin, lactose, calcium sulphate, compressible starch and any mixtures thereof;
said disintegrating agent is sodium carboxymethyl starch;
said binder is selected from the group consisting of an aqueous solution of polyvinyl pyrollidone with a mass concentration of 1%-10%, an ethanolic solution of polyvinyl pyrollidone with a mass concentration of 1%-10%, an aqueous solution of ethylcellulose with a mass concentration of 1%-10%, an ethanolic solution of ethylcellulose with a mass concentration of 1%-10%, an aqueous solution of hydroxypropyl methyl cellulose with a mass concentration of 1%-10%, and an aqueous solution of starch with a mass concentration of 1%-10%; and
said lubricant is selected from the group consisting of magnesium stearate, colloidal silicon dioxide, and talc.

2. The sustained-release tablet as claimed in claim 1, wherein said elemene is a mixture of β-elemene, gamma-elemene and delta-elemene, or is a β-elemene monomer.

3. The sustained-release tablet as claimed in claim 1, wherein said sustained-release agent is hydroxypropyl methyl cellulose or methyl cellulose.

4. The sustained-release tablet as claimed in claim 1, wherein said bulking agent is chosen from:
microcrystalline cellulose,
a mixture of microcrystalline cellulose and β-cyclodextrin,
a mixture of microcrystalline cellulose and lactose, and
a mixture of microcrystalline cellulose, β-cyclodextrin, and lactose.

5. The sustained-release tablet as claimed in claim 1, wherein said binder is an aqueous solution of starch with a mass concentration of 1%-10%.

6. The sustained-release tablet as claimed in claim 1, wherein said lubricant is colloidal silicon dioxide.

7. The sustained-release tablet as claimed in claim 1, wherein said sustained-release tablet consists essentially of:
10%-15% by weight of elemene in the total tablet;
3%-15% by weight of a sustained-release agent in the total tablet;
45%-70% by weight of a bulking agent in the total tablet;
3%-8% by weight of a sodium carboxymethyl starch in the total tablet;
1%-10% by weight of an aqueous solution of starch with a concentration of 1-10% in the total tablet; and
1%-8% by weight of a colloidal silicon dioxide in the total tablet;
said sustained-release agent is hydroxypropyl methyl cellulose or methyl cellulose; and
said bulking agent is selected from the group consisting of microcrystalline cellulose, the mixture of microcrystalline cellulose and lactose, and the mixture of microcrystalline cellulose and β-cyclodextrin and lactose.

8. The sustained-release tablet as claimed in claim 7, wherein said sustained-release tablet consists essentially of:
10%-12% by weight of elemene in the total tablet;
3%-8% by weight of a sustained-release agent in the total tablet;
61%-68% by weight of a bulking agent in the total tablet;
3%-6% by weight of a sodium carboxymethyl starch in the total tablet;
5%-8% by weight of an aqueous solution of starch with a concentration of 8% in the total tablet; and
5%-8% by weight of a colloidal silicon dioxide in the total tablet.

9. The sustained-release tablet as claimed in claim 7, wherein said bulking agent is the mixture of microcrystalline cellulose and lactose in a weight ratio ranging from 3:1 to 1:1; or said bulking agent is the mixture of microcrystalline cellulose, lactose and β-cyclodextrin, and the ratio of the total mass of microcrystalline cellulose and lactose to the mass of β-cyclodextrin is no less than 3:1.

10. The sustained-release tablet as claimed in claim 1, wherein said sustained-release tablet is made by weighing each component in the weight ratios set forth in claim 1; firstly mixing the bulking agent, the sustained-release agent and the disintegrating agent into homogeneity; then adding the binder for granulation; the resultant granulates being dried at a temperature of from 40° C. to 70° C., finished, sprayed evenly with the elemene, sealed to saturate for 20-60 minutes, dusted again with the lubricant, mixed homogenously, and pressed into tablets, thus resulting in said sustained-release tablets.

* * * * *